United States Patent
Brinkmann

(10) Patent No.: US 8,480,660 B2
(45) Date of Patent: Jul. 9, 2013

(54) DEVICE FOR THE TREATMENT OF BIOLOGICAL TISSUE USING LASER RADIATION

(75) Inventor: Ralf Brinkmann, Luebeck (DE)

(73) Assignee: Medizinisches Laserzentrum Luebeck GmbH, Luebeck (DE)

( * ) Notice: Subject to any disclaimer, the term of this patent is extended or adjusted under 35 U.S.C. 154(b) by 89 days.

(21) Appl. No.: 13/062,805

(22) PCT Filed: Sep. 9, 2009

(86) PCT No.: PCT/EP2009/006552
§ 371 (c)(1),
(2), (4) Date: Apr. 12, 2011

(87) PCT Pub. No.: WO2010/028822
PCT Pub. Date: Mar. 18, 2010

(65) Prior Publication Data
US 2011/0184393 A1 Jul. 28, 2011

(30) Foreign Application Priority Data
Sep. 9, 2008 (DE) .......................... 10 2008 046 394

(51) Int. Cl.
*A61B 18/20* (2006.01)
(52) U.S. Cl.
USPC .................................. 606/4; 606/10; 606/12
(58) Field of Classification Search
USPC ............ 606/4–6, 10–12; 607/88, 89; 128/898
See application file for complete search history.

(56) References Cited

U.S. PATENT DOCUMENTS
6,830,567 B2  12/2004  Schuele et al.

FOREIGN PATENT DOCUMENTS
DE   199 16 653 A1   10/2000
EP   1 279 385 A1    1/2003
WO   WO 01/97692 A1  12/2001

OTHER PUBLICATIONS

Jochen Kandulla, et al., "Noninvasive optoacoustic online retinal temperature determination during continuous-wave laser", Journal of Biomedical Optics, Jul./Aug. 2006, pp. 041111-1-041111-13, vol. 1, No. 4., XP002553666.
Kerstin Schlott, et al. "Optoacoustic Online Temperature Determination during Retinal Laser Photocoagulation", Therapeutic Laser Applications and Laser-Tissue Interactions III, Proceedings of the SPIE, 2007, pp. 66321B-1-66321B-8, vol. 6632, XP002553667.
International Search Report including partial translation dated Dec. 4, 2009 and PCT/ISA/237 Form (Ten (10) pages).
Corresponding Written Opinion of the International Searching Authority (Form PCT/ISA/237) with English translation, including Forms PCT/IB/338 and Form PCT/IB/373 (Seven(7) pages), Sep. 9, 2009.

*Primary Examiner* — Ahmed Farah
(74) *Attorney, Agent, or Firm* — Crowell & Moring LLP

(57) ABSTRACT

An apparatus for the treatment of biological, in particular living tissue comprising a treatment laser device 1 for generating a pulsed treatment radiation directed on to a target tissue, in an embodiment additionally including a measurement laser device 2, 3 for generating a pulsed measurement radiation directed on to the target tissue of lower energy and shorter pulse duration than the treatment radiation, a detector device 4 for measuring pressure transients induced by the measurement radiation and a control device 6 for controlling the treatment radiation in dependence on the pressure transients evaluated in respect of a tissue change, wherein a regulating or control algorithm for controlling the treatment radiation is formed from the pressure transients.

9 Claims, 2 Drawing Sheets

DEVICE FOR THE TREATMENT OF BIOLOGICAL TISSUE USING LASER RADIATION

BACKGROUND AND SUMMARY OF THE INVENTION

The invention concerns an apparatus for the treatment of biological tissue, in particular living tissue with laser radiation.

The therapeutic laser application to the eyeground, in particular in the case of retinal diseases, to achieve photocoagulation at the retina, is known. Lasers whose pulsed treatment radiation is in the green wavelength range are primarily used as treatment lasers in photocoagulation. That radiation is particularly strongly absorbed in the fundus layers of the eye. Solid state lasers, for example the frequency-doubled Nd:YAG laser of a wavelength of 532 nm are frequently used. Argon ion lasers at 514 nm are frequently also employed. The laser beams which are used in that case produce spot sizes of between 50 and 500 μm in the target tissue. The laser power levels can be up to several hundred mW, wherein irradiation durations of between 50 ms and 500 ms are employed. In the case of diabetic retinopathy panretinal photocoagulation, with the macula being cut out, is used, in which the treatment is performed over a large area with some hundred to over a thousand coagulation spots. In addition photocoagulation is used in relation to retinal holes and retina detachments. In that case a join between the retina and the eye background is produced in the edge regions of the retinal damage by scarring.

Hitherto the treatment parameters have been set on the basis of empirical values for dosing purposes. Because of different pigmentations in the eye the temperatures produced in the photocoagulation operation however may fluctuate to a greater or lesser degree.

EP 1 279 385 A1 discloses determining the temperature in the treatment of biological tissue in particular at the eyeground by means of laser radiation. In that case during the respective pulses of the pulsed treatment radiation additional radiation pulses of shorter pulse duration and lower energy level than in the treatment radiation are directed on to the target tissue. Tissue expansion and contraction phenomena which occur in that case produce bipolar pressure waves which are detected. Those measured pressure transients are used to ascertain the corresponding temperature values during the radiation treatment, with the aid of the Grüneisen calibration curve and a calibration temperature.

It is also known (DE 199 16 653 A1) to use the pressure transients generated in the target tissue as a measurement value for the optical properties of the target tissue in order thereby to control the further treatment procedure by comparison with especially ascertained characteristic curves in respect of the configuration of the changes in the optical properties during the therapy in fully automated on-line and computer-aided mode.

In photocoagulation however the tissue properties are modified at incipient denaturing of the target tissue, whereby the pressure amplitudes induced by the measurement radiations are also influenced.

The object of the invention is to provide an apparatus of the kind set forth in the opening part of this specification, in which the control of the treatment radiation is improved.

According to the invention that object is attained by an apparatus having the features of claim 1. The appendant claims recite advantageous developments of the invention.

In the invention the apparatus includes a device for generating a pulsed treatment radiation to be directed on to a target tissue, preferably a laser radiation. There is also a detector device for detecting pressure amplitudes coming from the target tissue. Those pressure amplitudes can be induced by the treatment radiation, in which case the treatment radiation is of a frequency of at least 100 Hz. It is also possible to additionally provide a measurement laser device for generating an additional pulsed measurement radiation directed on to the target tissue, of a lower energy level and a shorter pulse duration than in the case of the treatment radiation. In that case the detector device is suitable for detecting the pressure amplitudes induced by the measurement radiation and coming from the target tissue. There is also an evaluation device for evaluation of the pressure amplitudes detected by the detector device and a control device for controlling the treatment radiation in dependence on the evaluated pressure amplitudes.

In the treatment of the target tissue with the treatment radiation, in particular laser radiation, there is still no change in the tissue during a first, heating-up time interval $\Delta t_1$ in the target tissue. The duration of that first time interval can be for example 20-50 ms.

During the treatment with the treatment radiation, radiation is preferably effected with additional pulsed laser radiation, as is known from EP 1 279 385 A1. The pressure amplitudes which occur in that case increase with the time t during the interval $\Delta t_1$ on average in accordance with a function f(t).

The function m(t) represents the basic curvature characteristic of the temporal variation in the mean pressure amplitudes during the tissue heating-up phase in the absence of changes in the tissue. The function m(t) is known (Jochen Kandulla, Ralf Brinkmann, 'Nicht-invasive Echtzeit-Temperaturbestimmung während Laserbehandlungen an der Netzhaut des Auges': Photonic 2/2007, 42-46), it is based on the error function. It can be well approximated over short time intervals with different simpler functions. The function m(t) can be stored in a memory of the evaluation device or a memory connected to the evaluation device.

The fit factor a in accordance with the equation (f(t)=a*m(t) is unknown prior to measurement and is generally different in particular for each radiation location. The fit factor a depends on the probe laser energy and pigmentation of the area which is just being irradiated, but equally also on the propagation of sound in the eye, the acoustic impedance jump at the retina, the acoustic transducer geometry and sensitivity, signal amplification and so forth.

At each radiation location the averaged variation f(t) of the pressure amplitudes measured in the time interval $\Delta t_1$ is fitted with the fit factor a which occurs in that case in accordance with the fit condition f(t)=a*m(t). Accordingly a function a*m(t) is also available in a time region $\Delta t_2$ following the first time interval.

In $\Delta t_2$, at each moment in time t, the relationship of the currently prevailing measurement data function f(t) which reproduces the averaged variation in the measured pressure amplitudes and the function a*m(t) is formed. By virtue of the measurement data noise, a mean value of the currently prevailing measurement values f(t) (for example from 10 measurement values) can advantageously be related to the function a*m(t), for example as V(t)=f(t)/[a*m(t)].

For a change in the tissue and in particular tissue coagulation the evaluation device is so designed that it establishes whether and when a given predetermined deviation V* in the current measurement value f(t) from the function occurs in the second time interval $\Delta t_2$ following the first time interval (for example 20%, that is to say for example V*=0.8).

According to the invention establishing such a significant deviation during the time interval $\Delta t_2$ marks that tissue changes have occurred shortly before. Any continuation of the previous radiation would certainly produce even more severe tissue damage.

In particular the speed of implementation of tissue denaturing when irradiation is continued can be estimated from the moment in time $t_i$ at which the detected deviation V* occurs (that is to say $V(t_i)=V^*$). The radiation parameters of the treatment radiation for the third time interval $\Delta t_3$ which follows the second time interval are established from the moment in time $t_i$. They are afforded from previously experimentally obtained data. The experimentally ascertained data can be stored in a memory of the evaluation device or in a memory connected to the evaluation device.

The control circuit serving to control the treatment radiation can be adapted to control the duration and/or the power of the respective pulse of the treatment radiation. With the radiation power remaining the same the duration of $\Delta t_3$ is determined from the moment in time $t_i$ or the duration of $\Delta t_2$, wherein for example the duration of $\Delta t_3$ can be selected to be proportional to the duration of $\Delta t_2$. The shorter $\Delta t_2$ is, the correspondingly shorter is $\Delta t_3$.

The evaluation device is preferably in the form of a computer-aided evaluation device which includes corresponding memories for the function m(t) and the experimentally ascertained data required for control of the treatment radiation, in particular in the third time interval. This can involve data in respect of the processing time still to be applied and/or the power to be applied in respect of the treatment radiation. The invention makes it possible to use the measured pressure transients for control of the treatment radiation. In particular there is no need for calibration or standardisation to a temperature or other reference values.

BRIEF DESCRIPTION OF THE DRAWING FIGURES

The invention is described in greater detail with reference to the Figures in which.

DETAILED DESCRIPTION

Figure 1:
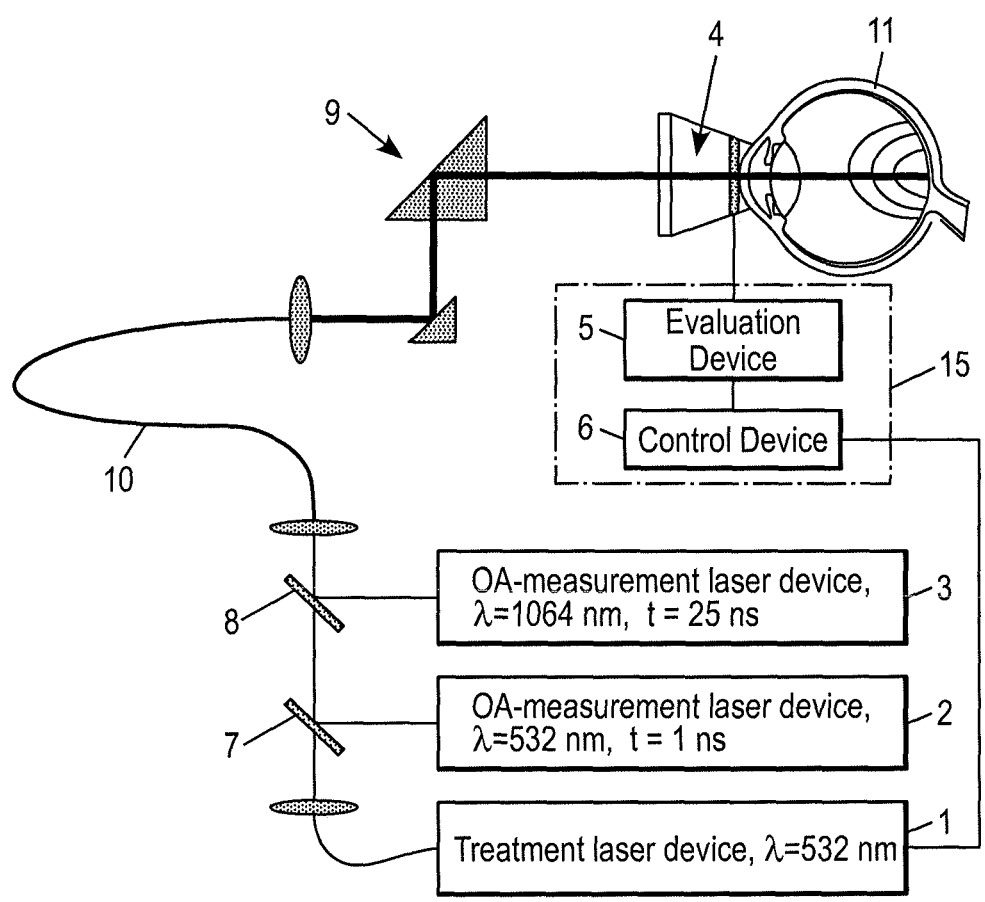
FIG. 1 shows an embodiment of the apparatus according to the invention.

FIG. 1 in the form of a schematic block circuit diagram shows an embodiment of the treatment apparatus. It includes a treatment laser device 1 having a treatment laser which emits pulsed treatment radiation in the green wavelength range, for example at a wavelength of 532 nm. A frequency-doubled Nd:YAG laser for example can be used for that purpose. An argon ion laser is also suitable, emitting pulsed treatment radiation at a wavelength of 514 nm. The spot sizes for the treatment beam incident on the target tissue can be between 10 μm and 1000 μm. The irradiation times for each radiation pulse can be between 30 ms and 500 ms or also higher. The laser power is selected in accordance with the respective treatment to be carried out at between 30 mW and over 1000 mW.

The illustrated apparatus further includes two measurement laser devices 2 and 3. The measurement laser device 2 includes a measurement laser which emits a pulsed measurement laser radiation in the green wavelength range, for example at a wavelength of 532 nm. That measurement laser radiation is coupled into the beam path of the treatment laser radiation by means of an optical coupler 7. The second measurement laser device 3 includes a measurement laser emitting pulsed measurement radiation in the infrared range, for example at a wavelength of 1064 nm. The measurement radiation is coupled into the beam path of the treatment radiation by means of an optical coupler 8. The pulse energy of the two measurement lasers is significantly less than that of the treatment radiation and is typically a few μJ. The pulse durations are also less than that of the treatment radiation by at least one hundred times.

As already described hereinbefore the two measurement radiations of the measurement laser devices 2 and 3 are coupled by means of the optical couplers 7 and 8 into the treatment radiation path coming from an optical fiber 10 from the treatment laser device 1. The treatment radiation and the measurement radiations are passed by way of a common optical fiber 10 into a slit lamp optical means 9 and directed from there on to the eyeground, for example the retina of an eye 11. That provides that the treatment radiation and the two measurement radiations are incident on the target tissue of the retina at the same spot. It is however also possible to use completely separate beam paths and correspondingly different spot diameters in the eye.

The pressure waves induced by the two measurement radiations are detected and measured by a detector 4. The detector 4 is fitted on to the cornea by means of a contact glass. EP 1 279 385 A1 describes various detector arrangements which can be used.

Instead of two measurement laser devices it is also possible to use only one measurement laser device. It is also possible to employ more than two measurement laser devices.

It is also possible to operate without measurement laser devices, that is to say only with the treatment laser device 1. In that case the frequency of the treatment radiation is so selected that evaluatable pressure amplitudes are detected by the detector device 4. In that case the frequency of the treatment radiation is at least 100 Hz. The pressure amplitudes induced by that radiation at the target tissue are then detected by the detector device 4 for evaluation thereof.

The pressure amplitudes measured by the detector device 4 (pressure transients) are passed to an evaluation device 5 and evaluated as will be described hereinafter. Control of the treatment laser device, in particular the treatment laser, is then effected by means of a control device 6 in dependence on evaluation.

Both the evaluation device 5 and also the control device 6 operate in computer-aided mode and can be implemented in an electronic computer device 15.

Figure 2:
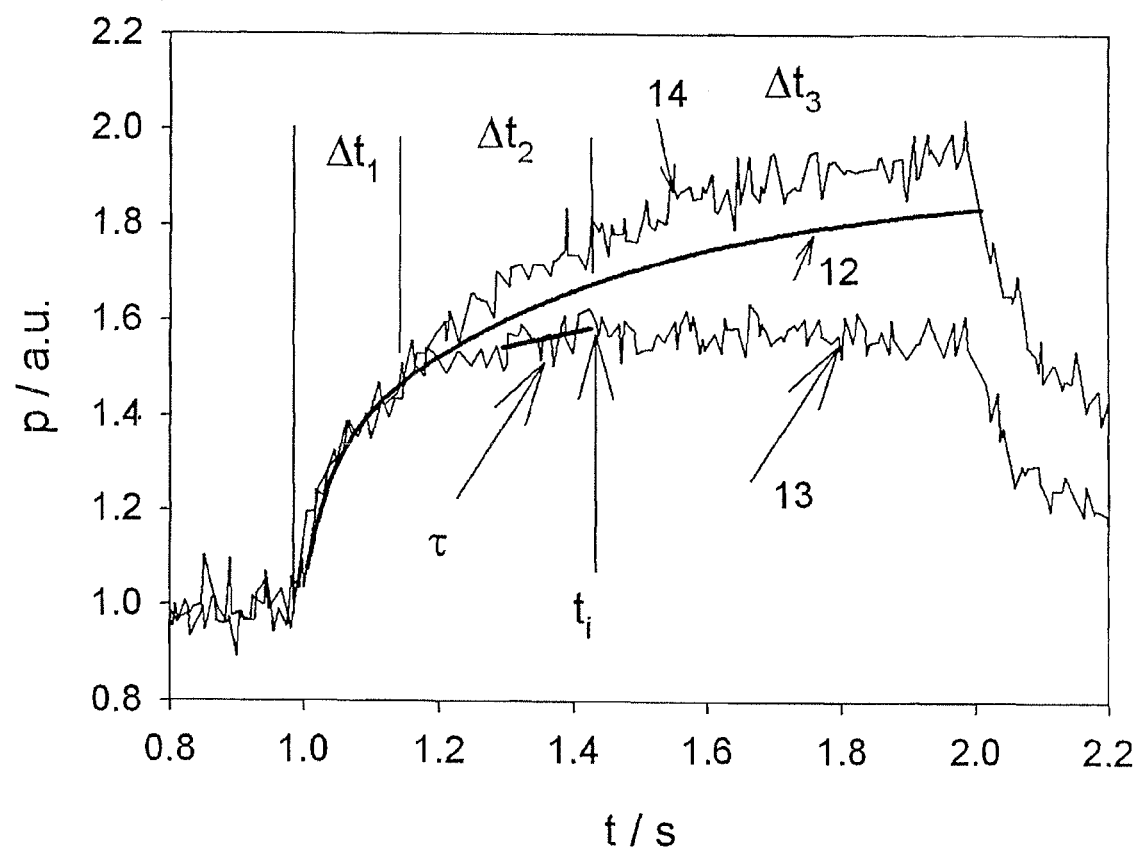
FIG. 2 shows a curve representation to illustrate the mode of operation of the FIG. 1 embodiment.

In FIG. 2 the variations in the pressure amplitudes induced by the two measurement radiations are plotted in relation to time t in seconds (s). With a constant pulse energy of the respective measurement laser and the treatment laser respectively, there is a rise in the pressure amplitudes by virtue of the temperature dependency of thermoelectric expansion, both for the pressure transients induced in the green wavelength range and also for the pressure transients induced in the infrared wavelength range. When using a treatment laser power which triggers tissue coagulation, for example a laser power of 180 mW, a substantially identical pressure rise occurs in respect of both induced pressure transients 13 and 14 within a first time interval $\Delta t_1$ in which still no photocoagulation occurs. The pressure transients 13 are the green-induced pressure transients and the pressure transients 14 are the infrared-induced pressure transients.

With commencing coagulation the variation in the green-induced pressure amplitudes shows a flattening-off while the infrared-induced pressure amplitudes continue to rise. The differing variation in the two pressure curves is due to the fact that the infrared measurement radiation penetrates more deeply into the fundus layer than the green measurement radiation. For the green ray which is strongly absorbed in the RPE, the scatter increases with ongoing coagulation in the retina and the RPE, which reduces absorption in the target tissue. In the infrared that effect also occurs but is weaker because of the higher wavelength. It is however over-compensated by the absorption, which is increased overall, in the choroidea, due to the reduced mean path length of a photon. The commencing photocoagulation of the tissue leads to pressure changes and deviations from the expected pressure configuration without a phase transition. That behaviour is utilised according to the invention in that a function a*m(t) with an algorithm which is as simple as possible is fitted to the currently measured pressure variation in the measurement data during the first time interval $\Delta t_1$. The curve 12 represents that function which is also used to control the treatment radiation. The first time interval $\Delta t_1$ is selected to be so short that it is certain that there are no changes in the irradiated tissue. That time interval can be for example 20-50 ms.

The averaged variation f(t) in the measurement data for the pressure transients induced by the measurement laser radiation in the first time interval $\Delta t_1$ is fitted with an algorithm which is as simple as possible in accordance with the fit condition f(t)=a*m(t). It will be appreciated that it is also possible to use complex imaging algorithms. The variation in the current measurement data function f(t) and a*m(t) are ascertained during the treatment radiation at a respective target tissue.

In the second time interval $\Delta t_2$ which follows the first time interval, the relationship V of the mean measurement value f(t) for the for example green-induced pressure transients with the function a*m(t) identified in FIG. 2 by reference 12 is formed at each moment in time. If the relationship V at a moment in time $t_i$ differs from V=1 by more than a predetermined relationship value, for example 20% (0.2) the second time interval $\Delta t_2$ is ended.

In the third time interval $Dt_3$ which begins at the moment in time $t_i$, it is possible to have recourse to tabled data which were previously ascertained experimentally. This involves in particular data for calculating the duration of the third time interval $Dt_3$ and possibly data for varying the power of the treatment radiation for a preselected coagulation strength.

With for example the power of the treatment radiation remaining the same the duration of the irradiation in the third time interval is selected to be proportional to the duration of the second time interval $\Delta t_2$ or proportional to the moment in time $t_i$.

The function m(t) used in the fit condition can be stored in the memory of the computer 15. The function m(t) is based on the aspect that the rise in the pressure amplitude as a function of the temperature at the irradiation location can be described as a good approximation with a second-degree polynomial. The development in respect of time of the increase in temperature as a consequence of the treatment radiation in turn theoretically follows from the error function as a solution to the heat diffusion equation (Jochen Kandulla, Ralf Brinkmann, 'Nicht-invasive Echtzeit-Temperaturbestimmung während Laserbehandlungen an der Netzhaut des Auges': Photonic 2/2007, 42-46).

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

List of References
1 treatment laser device
2 measurement laser device
3 measurement laser device
4 detector device
5 evaluation device
6 control device
7 coupler optical means
8 coupler optical means
9 slit lamp device
10 optical fiber
11 eye
12 fit function
13 green-induced pressure transients
14 infrared-induced pressure transients
15 electronic computer device

The invention claimed is:

1. An apparatus for the treatment of living tissue, comprising
a treatment device for generating a pulsed laser radiation to be directed on to a target tissue;
a detector device for detecting pressure amplitudes coming from the target tissue;
an evaluation device for evaluating the pressure amplitudes detected by the detector device; and
a control device for controlling the treatment radiation in dependence on the evaluated pressure amplitudes,
wherein
the evaluation device is adapted for evaluating a change of tissue condition in a second time interval $\Delta t_2$ which follows a first time interval $\Delta t_1$ in which no tissue change occurs at the target tissue, to determine a deviation of an averaged variation f(t) of the pressure amplitudes measured within the second time interval $\Delta t_2$ from a function a*m(t),
wherein m(t) represents a previously known curvature characteristic of the averaged temporal variation f(t) of the pressure amplitudes measured during the first time interval $\Delta t_1$ and a is determined from the fit condition f(t)=a*m(t) of a fit procedure at the end of $\Delta t_1$,
to determine a moment in time $t_i$ at which the deviation reaches a given value, and
in dependence on the determined moment in time $t_i$, to predetermine treatment radiation parameters for a third time interval $\Delta t_3$ following the second time interval $\Delta t_2$.

2. The apparatus as set forth in claim 1 wherein the control device is adapted to control the duration or the power of the respective pulse of the treatment radiation.

3. The apparatus as set forth in claim 1, wherein the evaluation device has a memory or is connected to a memory in which the curvature variation m(t) of the function f(t) is stored.

4. The apparatus as set forth in claim 1, wherein the evaluation device has a memory or is connected to a memory in which experimentally ascertained data are stored for predetermining the treatment parameters in the third time interval $\Delta t_3$.

5. The apparatus as set forth in claim 1, wherein the treatment duration in the third time interval $\Delta t_3$ is proportional to the duration of the second time interval $\Delta t_2$, and the power of the treatment radiation remains the same during the second and third time intervals.

6. The apparatus as set forth in claim 1, wherein in addition to the treatment device there is provided a measurement laser device for generating an additional pulsed measurement radiation directed on to the target tissue of lower energy and shorter pulse duration than in the case of the treatment radiation and the detector device is adapted to detect the pressure amplitudes induced by the measurement radiation and coming from the target tissue.

7. The apparatus as set forth in claim 1, wherein the detector device is adapted to detect the pressure amplitudes induced by the treatment radiation and coming from the target tissue.

8. The apparatus as set forth in claim 7 wherein the frequency of the treatment radiation is at least 100 Hz.

9. The apparatus as set forth in claim 1, wherein it is of a configuration for implementing photocoagulation at the fundus of an eye, in particular at the RPE.

\* \* \* \* \*